(12) United States Patent
Schueneman et al.

(10) Patent No.: US 7,305,884 B1
(45) Date of Patent: Dec. 11, 2007

(54) IN SITU MONITORING OF REACTIVE MATERIAL USING ULTRASOUND

(75) Inventors: Gregory T. Schueneman, Manchester, CT (US); George H. Temme, Cheshire, CT (US)

(73) Assignee: Henkel Corporation, Rocky Hill, CT (US)

( * ) Notice: Subject to any disclaimer, the term of this patent is extended or adjusted under 35 U.S.C. 154(b) by 168 days.

(21) Appl. No.: 11/107,832

(22) Filed: Apr. 18, 2005

Related U.S. Application Data (60) Provisional application No. 60/566,386, filed on Apr. 29, 2004.

(51) Int. Cl.
*G01N 29/00* (2006.01)

(52) U.S. Cl. .............................. 73/593; 73/599; 73/600; 73/602

(58) Field of Classification Search ................. 73/593, 73/599, 600, 602, 643, 644, 627, 628
See application file for complete search history.

(56) References Cited

U.S. PATENT DOCUMENTS

| | | | |
|---|---|---|---|
| 5,670,879 A | 9/1997 | Zombo et al. ............... 324/227 |
| 5,936,162 A | 8/1999 | Lingenberg et al. ........... 73/643 |
| 5,987,993 A | 11/1999 | Meier et al. .................... 73/643 |
| 6,487,909 B2 * | 12/2002 | Harrold et al. ................ 73/593 |
| 6,644,122 B2 * | 11/2003 | Borowczak et al. ........... 73/602 |
| 6,868,730 B2 * | 3/2005 | Kim et al. ..................... 73/643 |
| 6,924,642 B1 * | 8/2005 | Cho et al. ..................... 324/240 |
| 7,017,415 B2 * | 3/2006 | Harrold et al. ................ 73/702 |
| 7,017,418 B1 * | 3/2006 | Thakre et al. ................. 73/716 |
| 7,062,971 B2 * | 6/2006 | Harrold et al. ................ 73/593 |
| 7,134,591 B2 * | 11/2006 | Walther ....................... 228/104 |

* cited by examiner

*Primary Examiner*—Hezron Williams
*Assistant Examiner*—Jacques M. Saint-Surin
(74) *Attorney, Agent, or Firm*—Steven C. Bauman (57) ABSTRACT

The present invention provides a device and method of non-destructively monitoring reactive material through a substrate for changes in material properties that designate the condition of the reactive material during cure and service life. A transducer is placed on a portion of the substrate generally parallel to an interface of the substrate to the reactive material. The ultrasonic waves generated via the transducer are used to detect reflected sound waves upon encountering the interfaces, where the interfaces consist of changes in material properties across the substrate.

21 Claims, 8 Drawing Sheets

IN SITU MONITORING OF REACTIVE MATERIAL USING ULTRASOUND

CROSS REFERENCE TO RELATED APPLICATION

This application claims priority to U.S. Provisional Application No. 60/566,386, filed Apr. 29, 2004, the contents of which are incorporated herein by reference.

BACKGROUND OF THE INVENTION

1. Field of the Invention

The invention relates to an apparatus and method for producing ultrasonic waves for non-destructive monitoring of a reactive material, specifically, monitoring for changes in material properties that designate the condition of the reactive material during reaction and service life.

2. Brief Description of Related Technology

Ultrasonic velocity measurements are capable of nondestructively detecting material property changes in reactive materials such as adhesives, sealants, and coatings. Measurements of reflected ultrasonic waves have been shown to be sensitive to the changes that occur in silicone gasketing during accelerated aging. The change in sound velocity determined from these measurements correlate with changes in shear modulus, lapshear strength, and chemical degradation. The failure of such reactive materials is often preceded by similar changes in material properties. The detection of these changes during the service life of a reactive material would allow precise prediction of when repairs or replacements should be made.

Ultrasound, depending upon the frequency, can penetrate up to several inches or feet of metal, plastic, or ceramic. Thus, the capability to measure the sound velocity of a gasket or any reactive material is a possibility. Therefore, with the appropriate selection of ultrasonic transducer and analysis site the sound velocity can be measured and used to monitor changes in materials properties that directly indicate the condition of the material. Difficulty in obtaining sound velocity measurements arise when the target material concealed behind or within another material. This is a common occurrence in the applications that utilized adhesives, sealants, or coatings where the obscuring material is referred to as a substrate. Additionally, the substrates maybe irregular in shape such that no relatively flat area that is parallel to the bond line is available. This is commonly the case in engines as parts are molded to fit next to complex and irregular shapes and contours. This may prevent the implementation of ultrasound monitoring as will be discussed further below. Therefore, a need arises for having a specifically designed analysis port along the substrate that is flat and parallel to the reactive material such that sound velocity measurements can be conducted.

U.S. Pat. Nos. 5,987,993 and 5,936,162 show an apparatus and method for non-destructive material testing using electrodynamically generated ultrasonic waves. These patents include providing one or more radio frequency coils disposed in a uniform magnetic field placed parallel to a surface of the workpiece. A number of horizontally polarized ultrasound waves are produced in the workpiece due to interaction of the magnetic field with the currents supplied by the radio frequency coil.

U.S. Pat. No. 5,670,879 discloses a non-destructive inspection device and method for monitoring defects inside a turbine engine. Specifically, an ultrasound transducer or an eddy current sensor is used to generate a signal indicative of characteristics of the rotating member of the engine. That signal is compared to a known signal representation to identify the existence of a defective condition in the rotating member.

None of these patents overcome the need of designing the boundary of contact area of the reactive materials to the substrate to facilitate the inspection of the adhesive material properties via ultrasound.

SUMMARY OF THE INVENTION

The present invention provides an apparatus and method of non-destructively monitoring reactive material through a substrate for changes in material properties that designate the condition of the reactive material during cure and service life. The method includes prescribing a certain amount of thickness for the substrate. A transducer is placed on a portion of the substrate generally parallel to at least one interface of the substrate to the reactive material, where the interface being located in a portion of the substrate in contact with the reactive material. Further, ultrasonic waves are generated via the transducer to detect reflected sound waves received upon encountering the interfaces, where the interface includes changes in material properties across the substrate.

DETAIL DESCRIPTION OF THE INVENTION

Figure 1A:
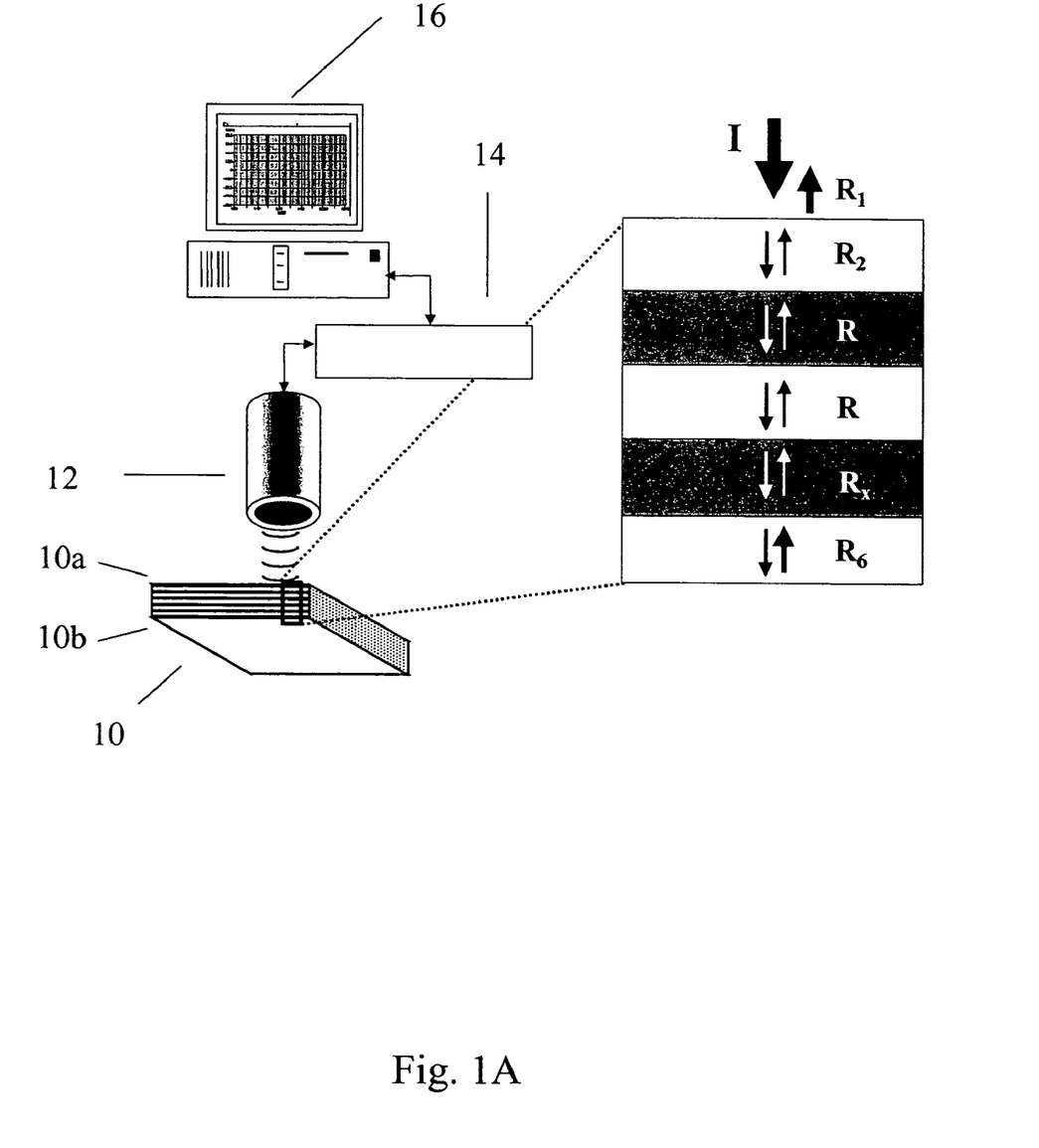
FIG. 1A shows a device for non-destructively monitoring reactive materials on a substrate using reflected sound waves.

Referring to FIG. 1A in accordance with one embodiment of the present invention, there is shown a device for non-destructively monitoring reactive materials on a substrate or a workpiece. The reactive material includes adhesive, coatings, and sealants, used in the substrate 10. The device includes a transducer 12 placed on a portion of the substrate 10 in such a manner that the face of the transducer 12 is parallel to an interface, where the interface is located in a surface of the substrate 10 in contact with the reactive material (not shown) as shown in FIG. 1A. The portion of the substrate 10 is an area of the substrate 10 where thickness and geometry are such that reflections within the substrate 10 and the reactive material can be resolved and the transversing ultrasonic waves are perpendicular to the interfaces. It is noted that a certain amount of thickness is prescribed for the substrate 10 and if necessary also for the reactive material in the substrate 10 to prevent overlapping of the sound reflections resulting in the interfaces as will be described in greater detail below. A pulser-receiver 14 also preferably excites the transducer 12 by emitting electrical spikes. The transducer 12 converts the electrical spike into ultrasonic waves and subsequently receives sound waves reflected by interfaces and converts them into electrical signals. These electrical signals are detected by the pulser-receiver 14. Additionally, a computer 16 receives or captures the waves in analog form from the pulser-receiver 14. The computer 16 digitizes the analog output of the pulser-receiver 14 and produces images of the relative intensity of the sound reflections encountered at the interfaces over a period of time. The intensity or frequency distribution of the reflected waves or the time between reflections, hence the sound velocity, are thus used to quantify and analyze the changes in material properties taking place in the reactive material. It is noted that the intensity and frequency distribution vary as material properties vary due to changes in sound dampening as will be described in greater detail below.

The interface is located in a portion of the substrate 10 which is in contact with the reactive material. The interface located between the substrate 10 make up the assembly between which the reactive material is contained. Some of the possible interfaces are transducer 12 to substrate 10, substrate 10 to contact area of the reactive material, subsequently the area of the reactive material to air (coating), or area of the reactive material 12 to the back of the substrate 10 (adhesive or sealant) interface. The interface consists of changes in material properties that produce a partial reflection and transmission of sound waves. These material properties include hardness, elastic modulus, density, geometry, homogeneity, and grain structure. These changes in material properties can be measured during reaction and service life to denote the degree of cure and aging, respectively. During the detecting and measuring the changes in material properties, the device preferably may encounter and detect flaws such as cracks, inclusions, corrosions, non-uniformities in homogeneities, and other flaws throughout the substrate and reactive material as will be discussed in greater detail below.

The portion of the substrate 10 on which the transducer 12 is placed is predesigned to be flat and parallel to the interfaces so that the transducer 12 can be securely placed on that portion such that the sound velocity can be measured and used to monitor changes in material properties that directly indicate the condition of a reactive material. Typically, a sound wave is launched by exciting the transducer 12 with either a voltage spike or a continuous wave impulse emitted by the receiver 14. These spikes are converted into vibrations, i.e., sound waves by the transducer 12. The transducer 12 generates and detects the ultrasonic waves traveling through the substrate 10 as shown in FIG. 1A. The ultrasonic waves generated by the transducer 12 are perpendicular to the interface. As shown in FIG. 1A as the waves travel from the top or outer surface 10a of the substrate 10 to the bottom surface 10b of the substrate 10, sound is reflected upon encountering an interface consisting for example of a change in stiffness or density from the medium it is traveling in. The sound waves reflected upon encountering the interfaces are captured by the receiver 14 and forwarded to the computer 16. Since these waves are in analog form, the computer 16 converts the analog output of the receiver 14 into digital format and further produces and displays the images preferably in graphical representation of reflection intensity over a period of time shown in FIG. 1B. The computer 16 also includes stored data such as prescribed thickness of the substrate 10 and the reactive material, knowledge of known reactive material changes in sound velocity with aging, and cure.

Figure 1B:
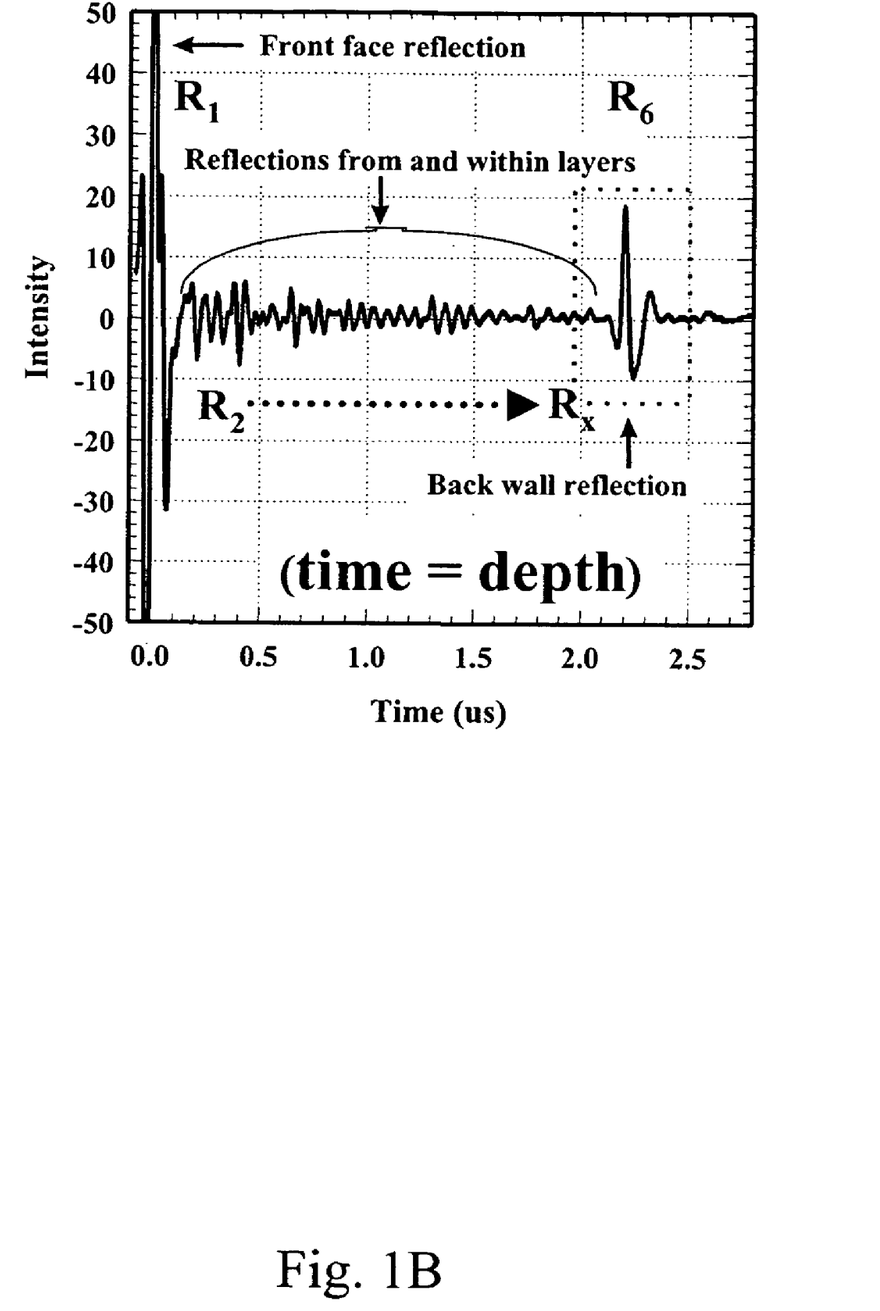
FIG. 1B illustrates a graphical representation of intensity versus time.

The reflection intensity determined by the change in material properties at each of the interfaces as the sound travels through the substrate 10 can be seen in the signal display of FIG. 1B produced by the computer 16. $R_1$ represents the front face of the substrate 10, $R_2$-$R_x$ represents the inside layers of the substrate 10 and $R_x$ represents the back wall portion of the substrate 10. As shown in FIG. 1B, the reflection intensity is high at the front face $R_1$ but falls down and remains steady at the reflections from and within layers $R_2$-$R_x$. Then, the reflection intensity increases at the reflection from the back wall $R_6$, however, the increase in intensity at $R_6$ is only about half the amount of the intensity at $R_1$. FIG. 1B shows the display of signal intensity versus time (us) with signals for each of the interfaces at $R_1$, $R_2$-$R_x$ and at $R_6$, respectively. The speed of sound in a homogenous medium is directly related to the material properties such as elastic modulus and density. Thus, changes in those material properties will affect pulse transit time through a substrate 10 of a prescribed or given thickness. Additionally, varying non-homogeneity may preferably also have an effect on sound velocity. The intensity of the reflection is directly proportional to the degree of change at the interface. It is these reflected waves that are primarily used in ultrasonic non-destructive testing. If the thickness (X) of the material transmitted between the two reflections is known then the sound velocity of the material (C) can be deduced using equation 1 below, where $\Delta t$ is the time interval between sound reflecting off of the top 10a and bottom surfaces 10b of the substrate 10. In most applications, this time interval $\Delta t$ is only a few microseconds or less. Clearly, $\Delta t$ plays a significant role in determining change in material properties of the reactive material. Additionally, the thickness must be multiplied by two due to sound transversing the sample twice to account for the down-and-back travel path.

$$C = \frac{2*X}{\Delta t} \tag{1}$$

As discussed above, it is necessary to know the thickness to calculate the sound velocity. However, if it is not feasible to control/know the thickness, it can be calculated from prior knowledge of the reactive material's sound velocity as a function of cure. This means measurements must be taken after assembly to monitor the reactive material for changes prior to service life to insure complete cure.

Figure 1C:
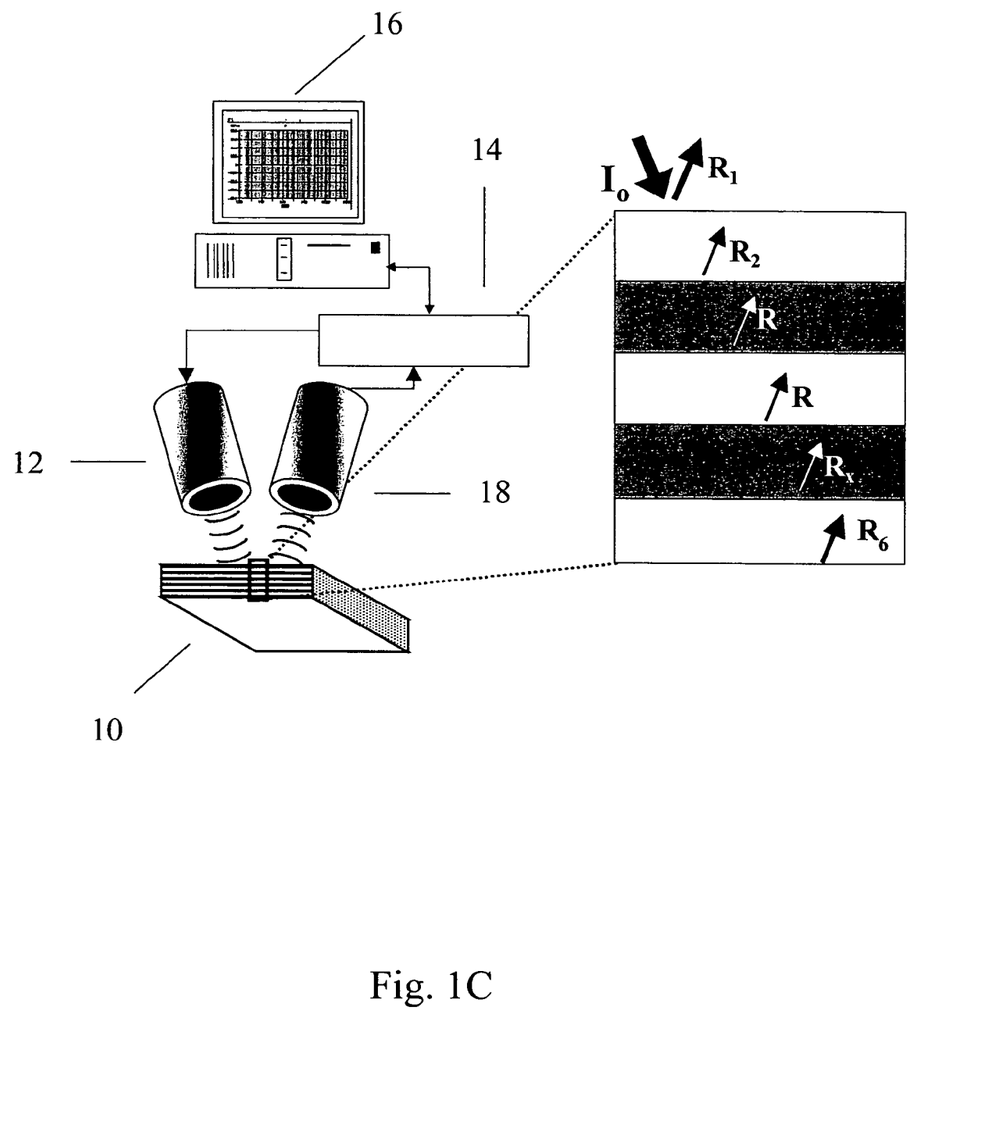
FIG. 1C illustrates a device for non-destructively monitoring reactive materials on a substrate using angularly reflected sound waves.
Figure 1D:
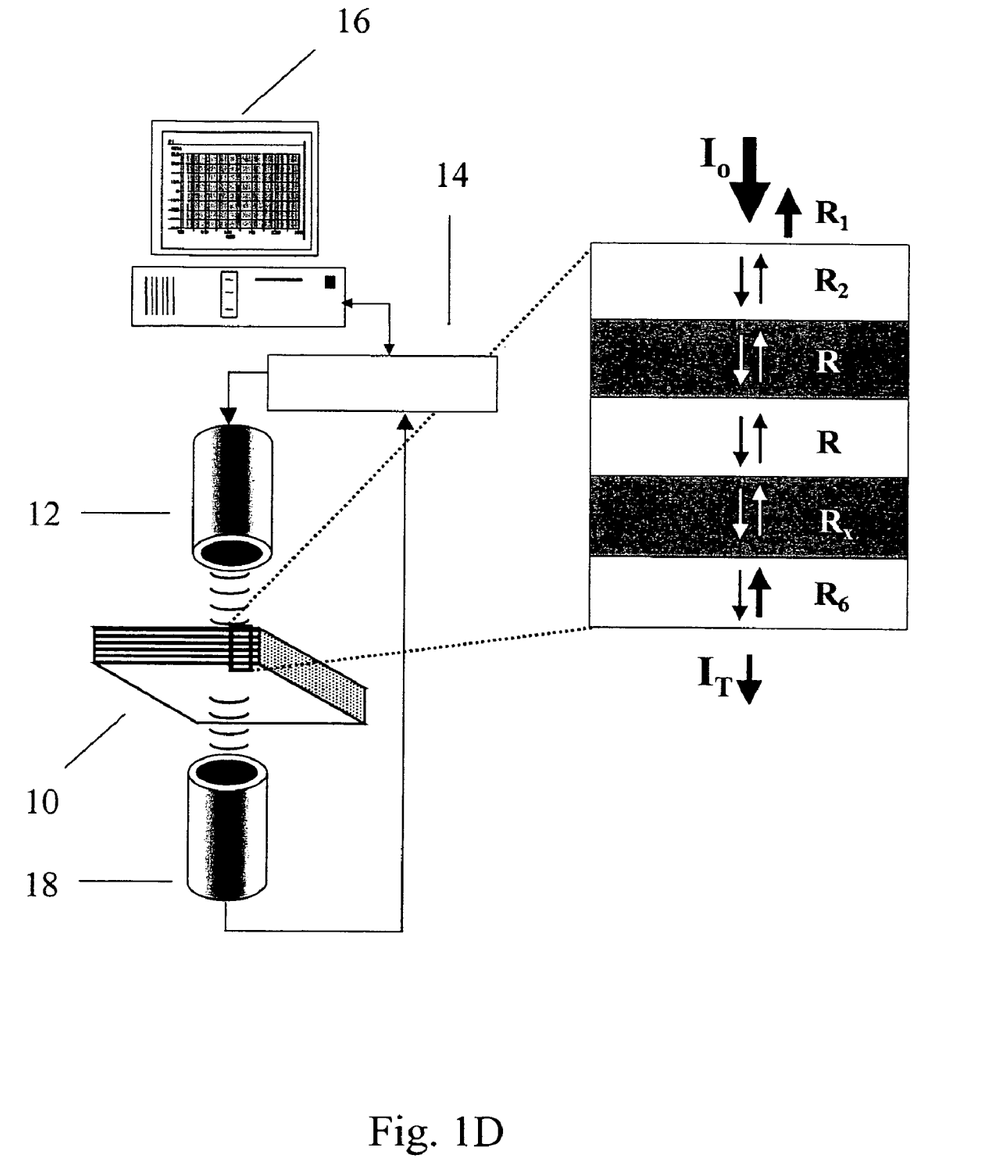
FIG. 1D illustrates a device for non-destructively monitoring reactive materials on a substrate using transmitted sound waves.

The preceding embodiment of the invention referring to FIG. 1A and FIG. 1B is generally for the case where the incident and reflected waves travel along the same route and a single transducer acts as both transmitter and receiver. In the second and third embodiments of the present invention, there are at least two other methods of detecting changes in said reactive materials that may be employed. One of the methods according to the second embodiment, utilize sound waves that are angularly reflected as shown in FIG. 1C. The other method according to the third embodiment, utilizes sound waves that are transmitted as shown in FIG. 1D. FIGS. 1C and 1D show devices for non-destructively monitoring reactive materials on a substrate or a workpiece using a second receiving transducer 18 to receive angularly reflected and transmitted sound waves, respectively. In these two cases the transmitting transducer 12 emits waves and the second transducer 18 detects them and sends corresponding electrical impulses to the pulser-receiver 14. Changes in the reactive material are determined by changes in the transit time, signal intensity, and frequency spectrum of the received sound waves. FIG. 1C is a special case of that shown in FIG. 1A and can be employed when for example the dimensions of the substrate 10 can not be altered. In FIG. 1C, the second receiving transducer 18 is aligned next to the transducer 12. So, this method requires the location of the second receiving transducer 18 to be aligned with the sound waves that are reflected upon interaction of the angular incident waves with one or more of the interfaces described previously. The transmitted wave method in FIG. 1D, can be employed when both the front and back surfaces of the substrate 10—reactive material assembly are accessible. In this case, the second receiving transducer 18 is aligned at the back surface of the substrate 10 across the transducer 12, which is employed at the front surface of the substrate. Here the total change in the transmitted sound waves will be representative of the changes in the reactive material during cure. Also, during service life, the changes in the transmitted sound waves will include the changes in the reactive material and the substrate. The utilization of angularly reflected or transmitted waves is a special case of reflected waves as discussed above. Even though the invention in the present application and the foregoing discussion is specific to reflected waves it is understood that the same is generally applicable to the two special cases with slight modification as discussed above.

Figure 2A:
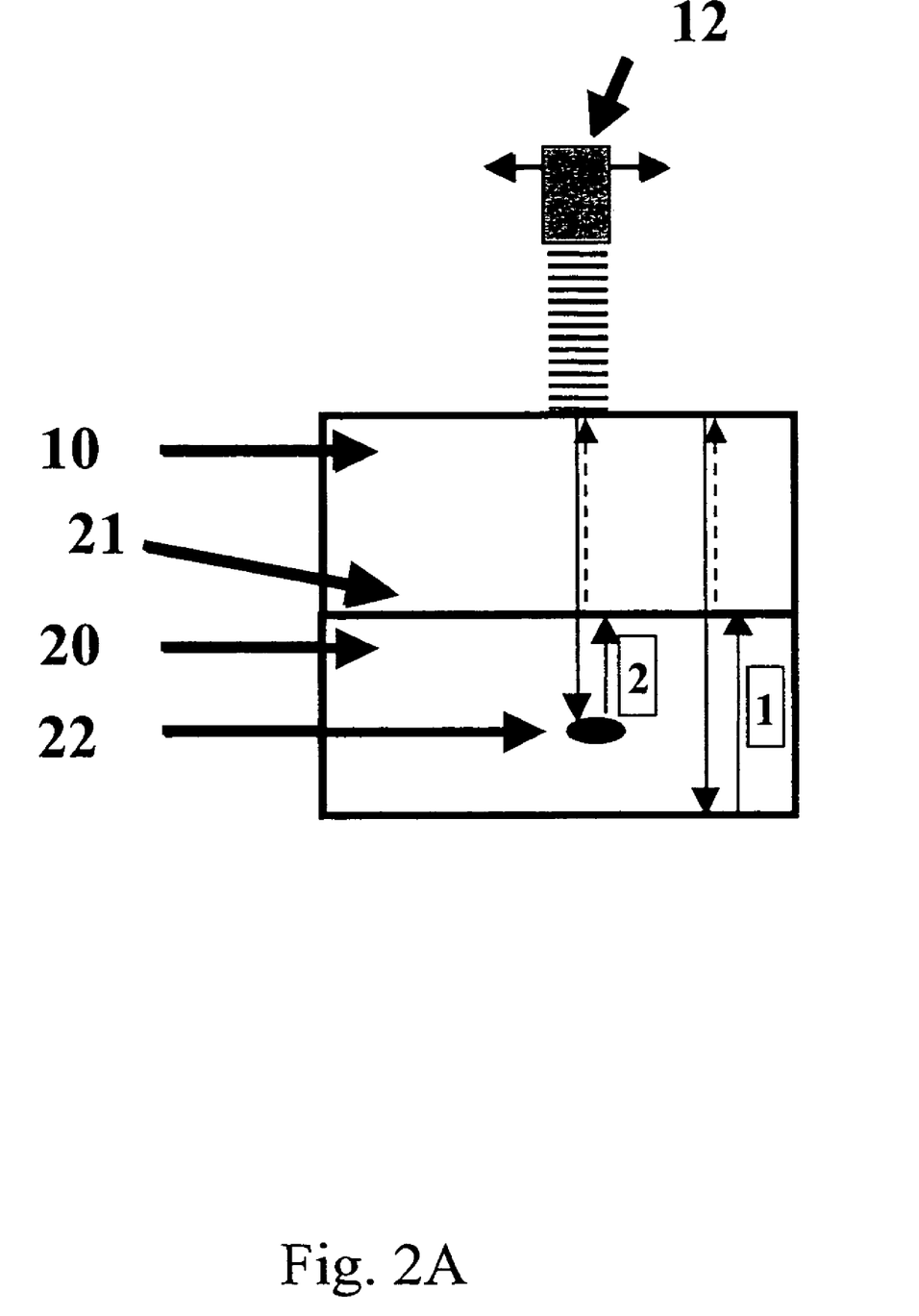
FIG. 2A illustrates a substrate in contact with a reactive material containing a flaw.
Figure 2B:
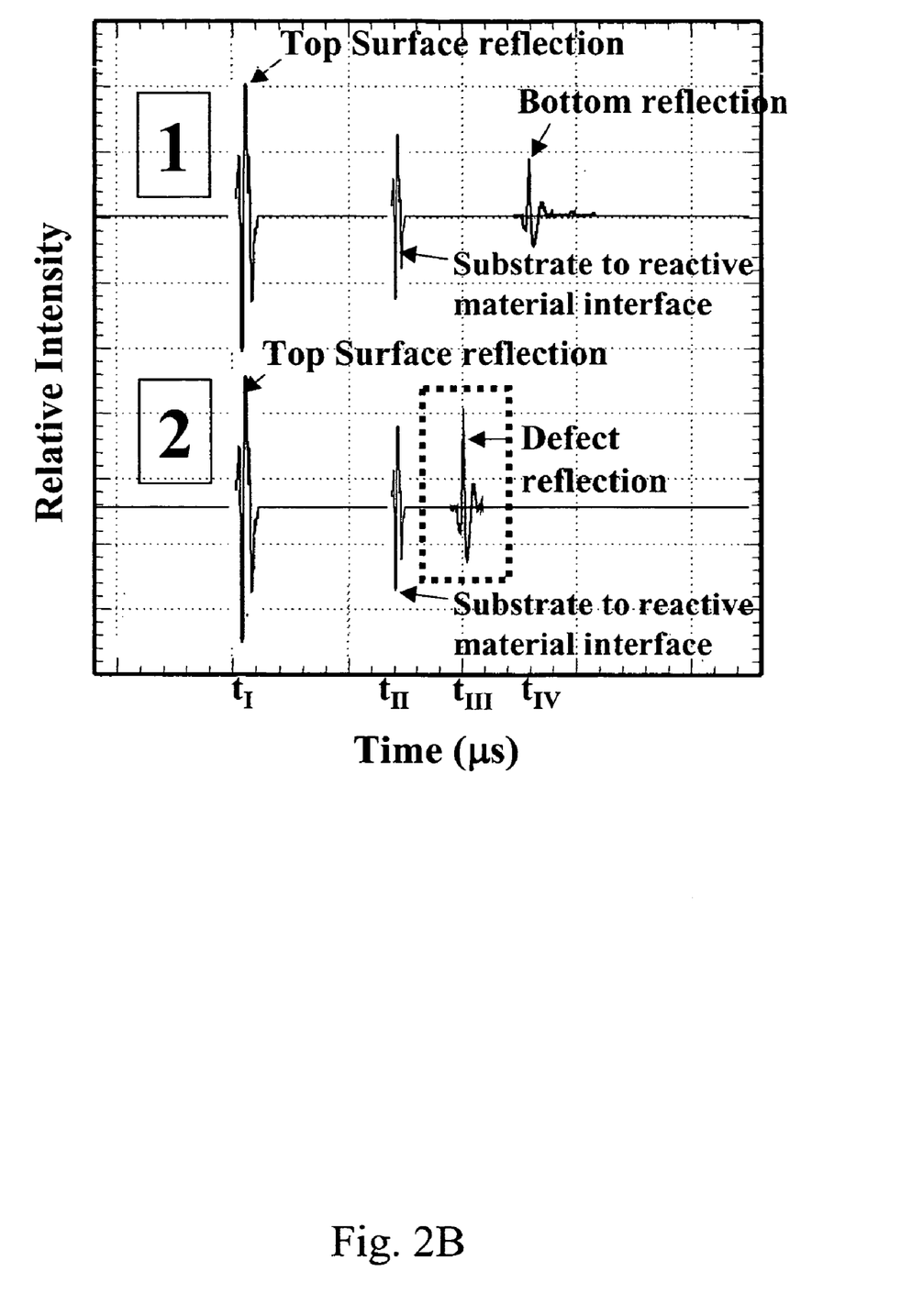
FIG. 2B illustrates a graphical representation of intensity versus time.

Referring to FIG. 2A of the present invention there is shown an ultrasonic evaluation of a substrate 10 in contact with a reactive material 20 containing a flaw 22. Position 1 in FIG. 2A shows a sound wave traveling from the top of the substrate 10 to the substrate 10 to reactive material interface 21 where a partial reflection and transmission occurs. The reflected wave returns to the transducer 12 and the transmitted wave travels to the bottom surface of the reactive material 20 and is partially reflected back to the transducer 12. Position 2 in FIG. 2A shows the sound wave behaving as described above except the transmitted portion from the substrate 10 to reactive material interface 21 encounters a defect 22 causing a portion of the wave to be reflected back to the transducer 12. FIG. 2B shows representative oscilloscope images of intensity and timing generated by a computer 16 of the reflected sound waves gathered from evaluation of positions 1 and 2. The image from position 1 shows a high intensity peak from the top surface of the substrate 10, a lower intensity peak from the substrate 10 to reactive material interface 21, and a lower intensity peak from the bottom surface of the reactive material 20. Knowledge of the thickness of the substrate 10 and reactive material 20 allows calculation of the sound velocity via equation 1. The image from position 2 shows a similar high intensity peak from the top surface of the substrate 10, and lower intensity peak from the substrate 10 to reactive material interface 21, but the reactive material's bottom surface peak has been replaced by one at approximately half the previous time. Since the substrate 10 and reactive material 20 has not undergone a change in thickness at position 2 the peak is due to a flaw 32 near the center of the reactive material's thickness. Flaws include cracks, inclusions, and corrosions, that may occur in the reactive material 20 and in the substrate 10. Upon detection of the flaw, there is clearly a change in sound velocity, thereby indicating change in material properties. Therefore, the failure of a reactive material can be preceded by the development of a internal flaw 32. The detection of flaws and material property changes both during the reaction and service life would allow precise prediction of when repairs or replacements should be made.

Figure 3A:
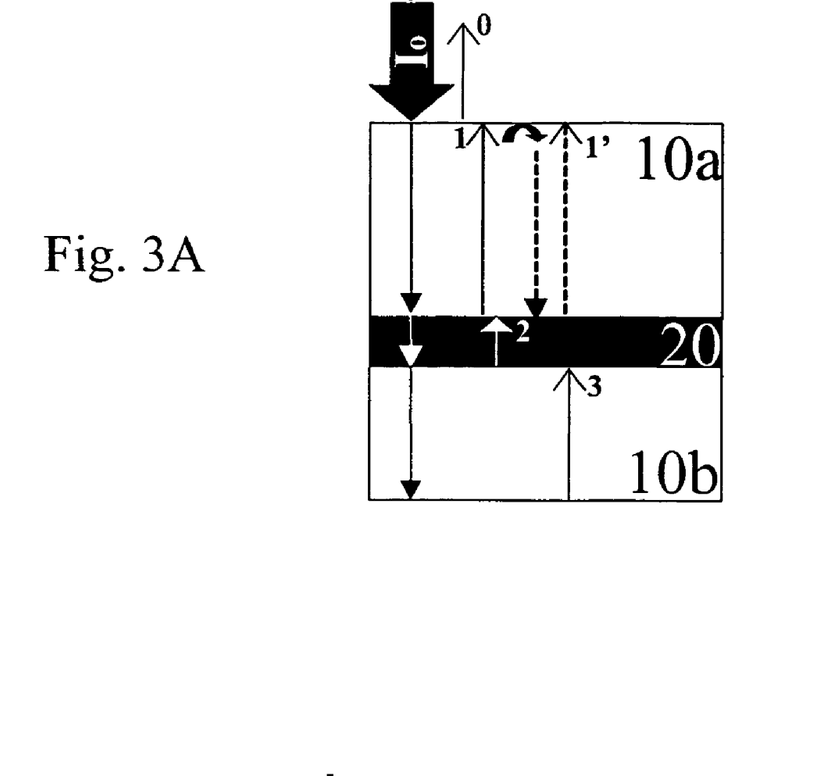
FIG. 3A illustrates a device for non-destructively monitoring flaws on a substrate.
Figure 3B:
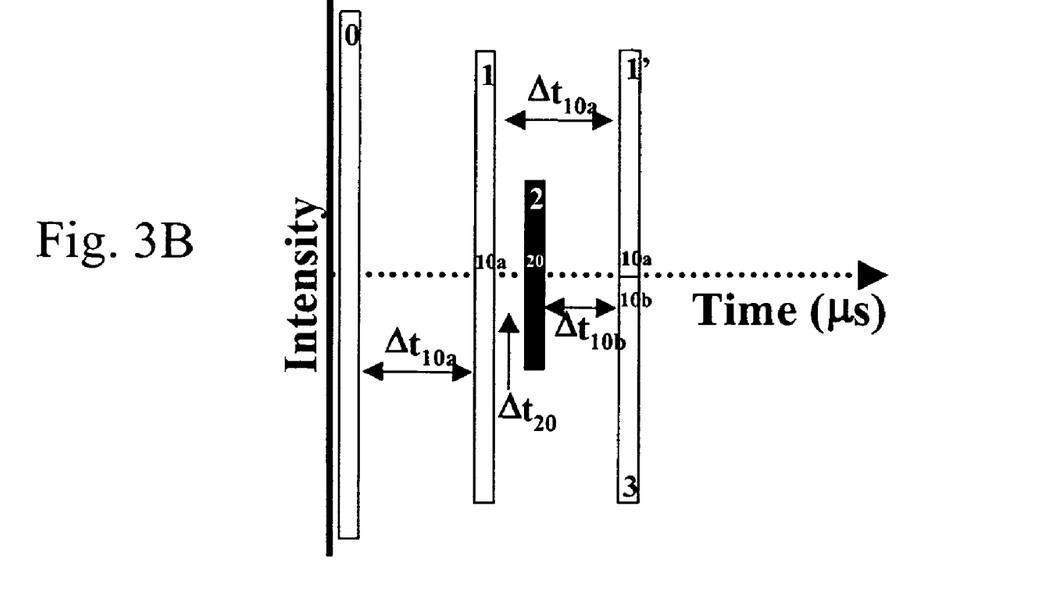
FIG. 3B illustrates a graphical representation of intensity versus time.

Since the substrate 10 shown in FIG. 1A as discussed above, is a multi-layered substrate, multiple reflections are received as shown in the display of FIG. 1B. Multiple material property interfaces normally exist in an adhesive, sealant, or coating assembly due to the multi-layer structure. A good example of this is shown in FIG. 3A where sound waves impinge ($I\circ$) on the outer substrate 10$a$ and transmit through the reactive material 20 to the bottom substrate 10$b$. A series of reflections is produced at each interface. These reflections are sequentially detected and displayed on the computer 16 as shown in FIG. 3B. The narrow rectangles represent the locations in time of each detected reflection. The order of the reflections is typical for an assembly with metal substrates. The dashed arrows in 10$a$ are from an internal reflection, a.k.a. reverberation, due to sound bouncing within it. This internal reflection (1') may appear near the same time as the reflection 2 from the reactive material 20 or reflection 3 from the bottom substrate 10$b$ as illustrated in FIG. 3A. Thus, care must be taken in specifying the thickness of 10$a$ to insure nothing interferes with reflection 2 from the reactive material 20.

Experiments are run to confirm the necessary dimensions of the portions of the substrate where the transducer is placed, such that no other signals interfere with that associated with the reactive material. As a guide, the timing of the individual peaks to avoid interference can be used to deduce the thickness to sound velocity relationships. Equation 2 below shows the necessary timing relationship for a signal from the reactive material to be clear of that from a second reflection 1' within substrate 10$a$. These times are shown in equation 3 below to be the sum of the necessary times for sound to transmit through objects above the bottom surface of the reactive material 20 layer. Since the time necessary to transmit through an object is equal to the ratio of the object's thickness and sound velocity, equation 3 can be converted to equation 4 below. Equation 4 allows the direct comparison of dimensions and material properties for a functioning portion of the substrate 10.

$$t_{20} < 2 * t_{10a} \tag{2}$$

$$\Delta t_{10a} + \Delta t_{20} < 2 * \Delta t_{10a} \tag{3}$$

$$\frac{X_{10a}}{C_{10a}} + \frac{X_{20}}{C_{20}} < 2 \frac{X_{10a}}{C_{10a}}, \text{ where } \left[\Delta t_i = \frac{X_i}{C_i}\right] \tag{4}$$

Figure 4:
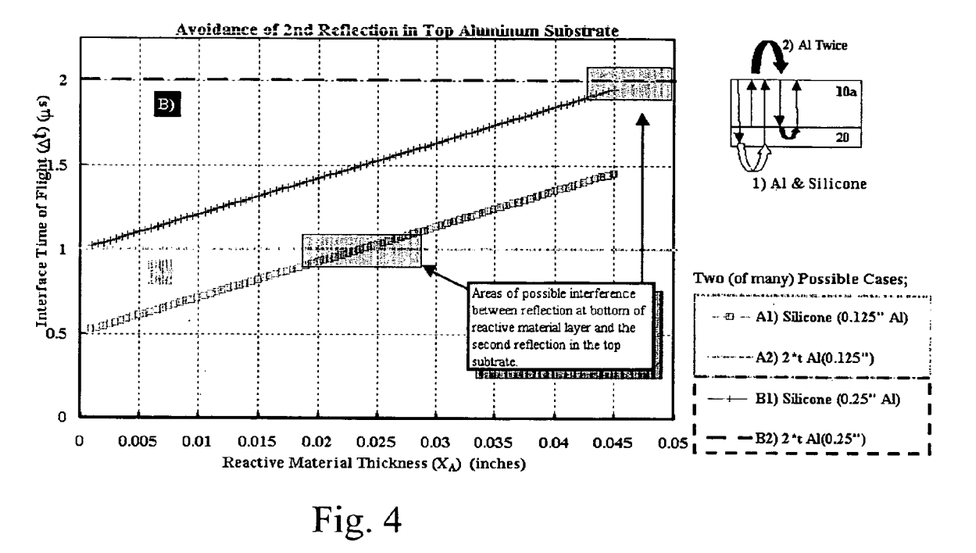
FIG. 4 illustrates the transit times of sound waves from the second reflection within an aluminum substrate and the first reflection from a non-contacting surface of the silicone reactive material.
Figure 5:
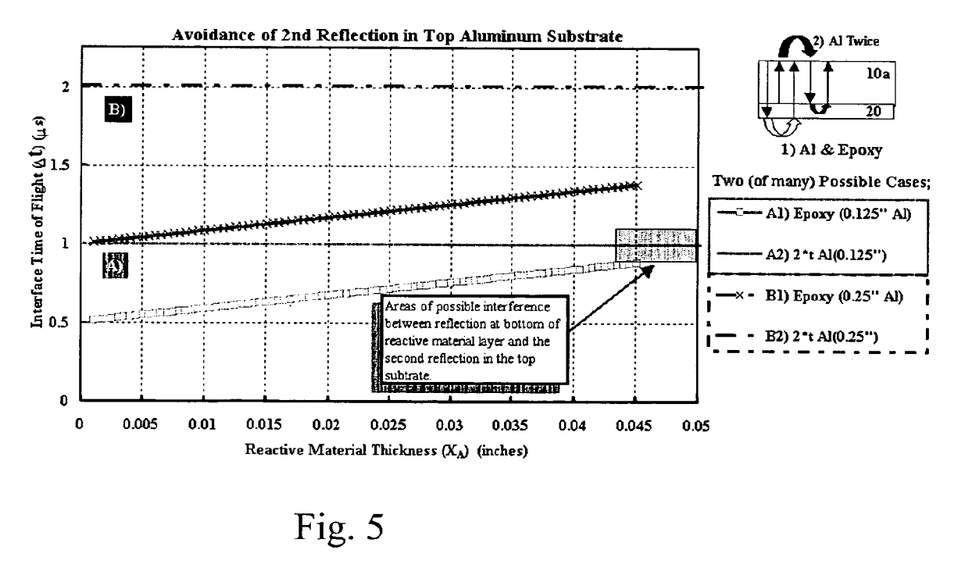
FIG. 5 illustrates the transit times of sound waves from the second reflection within an aluminum substrate and the first reflection from the non-contacting surface of the epoxy reactive material.

Assuming that equation 4 holds, a graphical representation of the allowable reactive material thickness for the given substrate 10 thickness are shown in FIGS. 4 and 5. FIG. 4 shows plot of time of flights for a second reflection within aluminum (C≅6320 m/s) and a first reflection within silicone (C≅1200 m/s) versus the thickness of the silicone. FIG. 5 shows a plot of time of flights for a second reflection within aluminum and a first reflection within epoxy (C≅3000 m/s) versus the thickness of the epoxy. Both figures show two cases where the aluminum has a thickness of 0.125" (A)

and 0.25 (B). In both FIG. 4 and FIG. 5, the gray boxes indicate areas of possible interference between reflection at bottom substrate 10b of reactive material 20 and second reflection in the top substrate 10a. The dimensions of these boxes represent the contributions from the widths of the reflected signals, which are not taken into account in the plotted lines. These plots are for a general guide only because they do not take into account other possible signals that may be present in the work piece. Experiments are run to confirm a selected geometry works before it is implemented.

What is claimed is:

1. A method of non-destructively monitoring reactive material through a substrate for changes in material properties that designate the condition of the reactive material during cure and service life, said method comprising the steps of:
    (a) prescribing a certain amount of thickness for the substrate;
    (b) placing a transducer on a portion of the substrate generally parallel to at least one interface of the substrate and the reactive material, said interface being located in a surface of the substrate in contact with the reactive material;
    (c) generating ultrasonic waves with the transducer that travel through the substrate and are reflected on encountering an interface; and
    (d) detecting and determining whether the reflected sound waves indicate changes in material properties of the reactive material.

2. The method of claim 1 wherein said reactive material includes adhesives, coatings, sealants and combinations thereof.

3. The method of claim 1 wherein said material properties include modulus, density, thickness, geometry and combinations thereof.

4. The method of claim 1 wherein said ultrasonic waves generated are perpendicular to the interfaces.

5. The method of claim 1 further comprising receiving the ultrasonic waves reflected upon encountering an interface and determining whether the reflected sound waves indicate changes in material properties of the reactive material with a computer that analyzes at least one of the intensity, frequency distribution, or time between reflections of the reflected sound waves.

6. The method claim 1 further comprising detecting flaws in reactive materials through said substrate.

7. The method of claim 6 wherein said flaws include cracks, inclusions, corrosions, non-uniformities, inhomogeneities and combinations thereof.

8. The method of claim 1, wherein the material properties include the cure state of the reactive material.

9. The method of claim 1, wherein the reactive material is concealed behind the substrate.

10. The method of claim 1, further comprising predicting when repairs or replacements of reactive materials should be performed.

11. The method of claim 1, further comprising detecting the physical failure of reactive materials.

12. An assembly for non-destructively monitoring reactive material through a substrate with at least one interface, comprising:
    (a) a transducer placed on a portion of the substrate wherein the face of the transducer is parallel to at least one interface of the substrate and the reactive material, said interface being located in a surface of the substrate in contact with the reactive material;
    (b) generating ultrasonic waves with the transducer that travel through the substrate and are reflected on encountering an interface; and
    (c) detecting and determining whether the reflected sound waves indicate changes in material properties of the reactive material.

13. The assembly of claim 12 wherein the computer displays the intensity, frequency distribution, and time between reflections at each interface.

14. The assembly of claim 12 wherein the computer quantifies and analyzes at least one of the intensity, frequency distribution, or time between reflections at each interface to determine a degree of change in material properties of the reactive material.

15. The assembly of claim 12, further comprising stored data in the computer, including a prescribed thickness of the substrate and reactive material.

16. The assembly of claim 12, further comprising stored data in the computer, including known changes in intensity, frequency distribution, and time between reflections due to flaws or the cure state in the reactive material.

17. A system for non-destructively monitoring a reactive material on a substrate comprising:
    (a) a first transducer placed on a portion of the substrate wherein the face of the transducer is parallel to an interface of the substrate and the reactive material, said interface being located in a surface of the substrate in contact with the reactive material;
    (b) a second transducer positioned next to the first transducer, wherein said second transducer is aligned so that the sound waves reflected upon the interaction of angular incident waves generated by the first transducer upon encountering an interface are detected by the second transducer;
    (c) detecting and determining whether the reflected sound waves indicate changes in material properties of the reactive material.

18. The system of claim 17 wherein the computer displays the intensity, frequency distribution, and time between reflections at each interface.

19. The system of claim 17 wherein the computer quantifies and analyzes at least one of the intensity, frequency distribution, or time between reflections at each interface to determine a degree of change in material properties of the reactive material.

20. A system for non-destructively monitoring a reactive material on a substrate with a front and back surface, comprising:
    (a) a first transducer placed on the front surface of the substrate wherein the face of the transducer is parallel to an interface of the substrate to the reactive material, said interface being located in a surface of the substrate in contact with the reactive material;
    (b) a second transducer positioned on the back surface of the substrate, aligned to detect sound waves transmitted by the first transducer upon encountering said interface; and
    (c) detecting and determining whether the reflected sound waves indicate changes in material properties of the reactive material.

21. The system of claim 20 further comprising a prescribed thickness of the substrate and the reactive material.

* * * * *